United States Patent
Bradley et al.

(10) Patent No.: US 8,401,665 B2
(45) Date of Patent: *Mar. 19, 2013

(54) APPARATUS AND METHODS FOR DETECTING POSITION AND MIGRATION OF NEUROSTIMULATION LEADS

(75) Inventors: Kerry Bradley, Glendale, CA (US); Sunil K. Kapoor, Pasadena, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 2096 days.

This patent is subject to a terminal disclaimer.

(21) Appl. No.: 11/096,662

(22) Filed: Apr. 1, 2005

(65) Prior Publication Data

US 2006/0224187 A1    Oct. 5, 2006

(51) Int. Cl.
*A61N 1/00* (2006.01)
(52) U.S. Cl. .......................................... 607/62
(58) Field of Classification Search ............... 607/45, 607/48, 27, 28, 37, 62
See application file for complete search history.

(56) References Cited

U.S. PATENT DOCUMENTS

| | | |
|---|---|---|
| 3,646,940 A | 3/1972 | Timm et al. |
| 3,724,467 A | 4/1973 | Avery et al. |
| 3,822,708 A | 7/1974 | Zilber |
| 4,552,150 A | 11/1985 | Zacouto |
| 4,735,204 A | 4/1988 | Sussman et al. |
| 4,911,174 A | 3/1990 | Pederson et al. |
| 5,184,624 A | 2/1993 | Brown et al. |
| 5,201,865 A | 4/1993 | Kuehn |
| 5,333,618 A | 8/1994 | Lekhtman et al. |
| 5,702,429 A | 12/1997 | King |
| 5,735,887 A | 4/1998 | Barreras, Sr. et al. |
| 5,814,088 A | 9/1998 | Paul et al. |
| 5,814,092 A | 9/1998 | King |
| 5,895,416 A | 4/1999 | Barreras, Sr. et al. |
| 5,913,882 A | 6/1999 | King |
| 5,941,906 A | 8/1999 | Barreras, Sr. et al. |
| 6,027,456 A | 2/2000 | Feler et al. |
| 6,050,267 A | 4/2000 | Nardella et al. |
| 6,052,624 A | 4/2000 | Mann |
| 6,181,969 B1 | 1/2001 | Gord |
| 6,195,584 B1 | 2/2001 | Hill et al. |
| 6,269,268 B1 | 7/2001 | Callaghan et al. |
| 6,353,762 B1 | 3/2002 | Baudino et al. |
| 6,381,496 B1 | 4/2002 | Meadows et al. |
| 6,393,325 B1 | 5/2002 | Mann et al. |
| 6,490,486 B1 | 12/2002 | Bradley |
| 6,516,227 B1 | 2/2003 | Meadows et al. |
| 6,587,724 B2 | 7/2003 | Mann |

(Continued)

FOREIGN PATENT DOCUMENTS

| WO | WO-02/09808 A1 | 2/2002 |
|---|---|---|
| WO | 2006107848 A2 | 10/2006 |

OTHER PUBLICATIONS

PCT International Search Report for PCT/US2006/012258, Applicant: Advanced Bionics Corporation, Form PCT/ISA210 and 220, dated Sep. 25, 2006 (6 pages).

(Continued)

*Primary Examiner* — Scott Getzow
(74) *Attorney, Agent, or Firm* — Vista IP Law Group LLP (57) ABSTRACT

Apparatus and methods for detecting lead migration through the use of measured artifactual data about the tissue in the vicinity of the lead.

27 Claims, 6 Drawing Sheets

U.S. PATENT DOCUMENTS

| | | | |
|---|---|---|---|
| 6,609,029 | B1 | 8/2003 | Mann et al. |
| 6,662,053 | B2 | 12/2003 | Borkan |
| 6,721,600 | B2 | 4/2004 | Jorgenson et al. |
| 6,741,892 | B1 | 5/2004 | Meadows et al. |
| 6,913,763 | B2 | 7/2005 | Lerner |
| 6,993,384 | B2 | 1/2006 | Bradley |
| 7,239,920 | B1 | 7/2007 | Thacker et al. |
| 7,317,948 | B1 | 1/2008 | King et al. |
| 7,412,287 | B2 | 8/2008 | Yonce et al. |
| 7,582,062 | B2 | 9/2009 | Magill et al. |
| 7,664,550 | B2 | 2/2010 | Eick et al. |
| 8,131,357 | B2 * | 3/2012 | Bradley et al. .................... 607/2 |
| 2001/0049543 | A1 | 12/2001 | Kroll |
| 2003/0139781 | A1 | 7/2003 | Bradley et al. |
| 2003/0153959 | A1 | 8/2003 | Thacker et al. |
| 2004/0049235 | A1 | 3/2004 | Deno et al. |
| 2004/0064161 | A1 * | 4/2004 | Gunderson et al. ............. 607/28 |
| 2004/0078067 | A1 | 4/2004 | Thompson et al. |
| 2004/0082978 | A1 | 4/2004 | Harrison et al. |
| 2004/0116978 | A1 | 6/2004 | Bradley |
| 2004/0172083 | A1 | 9/2004 | Penner |
| 2005/0055065 | A1 | 3/2005 | Campbell |
| 2006/0224187 | A1 | 10/2006 | Bradley et al. |

OTHER PUBLICATIONS

PCT Written Opinion of the International Search Authority for PCT/US2006/012258, Applicant Advanced Bionics Corporation, Form PCT/ISA/237, dated Sep. 25, 2006 (9 pages).

King et al., U.S. Appl. No. 10/364,434, filed Feb. 11, 2003 and entitled "Neural Stimulation System Providing Auto Adjustment of Stimulus Output as a Function of Sensed Pressure Changes."

Thacker et al., U.S. Appl. No. 10/364,436, filed Feb. 11, 2003 and entitled "Neural Stimulation System Providing Auto Adjustment of Stimulus Output as a Function of Sensed Impedance."

Bradley, "System and Method for Determining Distances From Electrodes to Neural Tissue," published Feb. 12, 2004 by IP.Com (IPCOM000021845D).

Office Communication dated Jan. 8, 2008 from related U.S. Appl. No. 11/096,483, filed Apr. 1, 2005; Kerry Bradley (25 pages).

Office Communication dated Feb. 1, 2008 from related European application Serial No. 06 740 372.5-1265; Applicant: Advanced Bionics Corporation (4 pages).

PCT International Preliminary Report for PCT/US2006/012258, Applicant: Advanced Bionics Corporation, Forms PCT/IB373 and PCT/ISA237, dated Oct. 11, 2007 (11 pages).

File History of U.S. Appl. No. 11/096,483, filed Apr. 1, 2005, Inventor: Kerry Bradley.

Office Action dated Aug. 5, 2008 in U.S. Appl. No. 11/096,483, filed Apr. 1, 2005, Inventor: Kerry Bradley (13 pages).

Office Action dated Nov. 7, 2008 in U.S. Appl. No. 11/096,483, filed Apr. 1, 2005, Inventor: Kerry Bradley (12 pages).

Office Action dated Apr. 27, 2009 in U.S. Appl. No. 11/096,483, filed Apr. 1, 2005, Inventor: Kerry Bradley (14 pages).

Office Action dated Sep. 15, 2009 in U.S. Appl. No. 11/096,483, filed Apr. 1, 2005, Inventor: Kerry Bradley (14 pages).

Office Action dated Feb. 19, 2010 in U.S. Appl. No. 11/096,483, filed Apr. 1, 2005, Inventor: Kerry Bradley (13 pages).

Office Action dated Aug. 3, 2010 in U.S. Appl. No. 11/096,483, filed Apr. 1, 2005, Inventor: Kerry Bradley (14 pages).

Office Action dated Feb. 8, 2011 in U.S. Appl. No. 11/096,483, filed Apr. 1, 2005, Inventor: Kerry Bradley (15 pages).

Office Action dated Jun. 22, 2011 in U.S. Appl. No. 11/096,483, filed Apr. 1, 2005, Inventor: Kerry Bradley (10 pages).

Office Action dated Aug. 22, 2011 in U.S. Appl. No. 11/096,483, filed Apr. 1, 2005, Inventor: Kerry Bradley (8 pages).

Notice of Allowance dated Oct. 31, 2011 in U.S. Appl. No. 11/096,483, filed Apr. 1, 2005, Inventor: Kerry Bradley (5 pages).

PTO Communication dated Dec. 16, 2011 in U.S. Appl. No. 11/096,483, filed Apr. 1, 2005, Inventor: Kerry Bradley (4 pages).

Office Communication dated Oct. 24, 2011 in Japanese Patent Application No. 2008-504490, Applicant: Boston Scientific Neuromodulation Corporation (3 pages) including Partial English Translation (3 pages).

* cited by examiner

FIG. 6A
Baseline Positions

FIG. 6B
Subsequent Positions

FIG. 7

FIG. 8A Baseline Positions

FIG. 8B Subsequent Positions

APPARATUS AND METHODS FOR DETECTING POSITION AND MIGRATION OF NEUROSTIMULATION LEADS

BACKGROUND OF THE INVENTIONS

1. Field of Inventions

The present inventions relate generally to neurostimulation systems.

2. Description of the Related Art

Neurostimulation systems, such as spinal cord stimulation (SCS) systems, deep brain stimulation systems and subcutaneous stimulation systems, include electrodes that are positioned adjacent to neural elements that are the stimulation target. The electrodes are commonly mounted on a carrier and, in many instances, a plurality of electrodes are mounted on a single carrier. These carrier/electrode devices are sometimes referred to as "leads." Because the proper placement of the electrodes is critical to the success of neurostimulation therapy, the surgeon will carefully position one or more leads such that the electrodes are adjacent to the target neural elements. There will typically be 1 to 5 mm between adjacent leads.

Stimulation energy is delivered to the electrodes during and after the placement process in order to verify that the electrodes are stimulating the target neural elements. Stimulation energy is also delivered to the electrodes at this time to formulate the most effective stimulus pattern (or regimen). The pattern will dictate which of the electrodes are sourcing or returning current pulses at any given time, as well as the magnitude and duration of the current pulses. The stimulus pattern will typically be one that provides stimulation energy to all of the target tissue that must be stimulated in order to provide the therapeutic benefit (e.g. pain relief), yet minimizes the volume of non-target tissue that is stimulated. Thus, neurostimulation leads are typically implanted with the understanding that the stimulus pattern will require fewer than all of the electrodes on the leads to achieve the desired "paresthesia," i.e. a tingling sensation that is effected by the electrical stimuli applied through the electrodes.

A wide variety of leads have been introduced. One common type of neurostimulation lead is the "in-line" lead, which includes a plurality of spaced electrodes on a small diameter carrier. In-line leads are relatively easy to place because they can be inserted into the spinal canal through a percutaneous needle in a small locally-anesthetized incision while the patient is awake and able to provide feedback. In-line leads are also advantageous because they can be removed relatively easily. One of the disadvantages of in-line leads is that they are prone to migrating in the epidural space, either over time or as a result of a sudden flexion movement.

Lead migration can result in the targeted neural elements no longer being appropriately stimulated and the patient no longer realizing the full intended therapeutic benefit. Lead migration is, however, not the only reason that the therapeutic effects of a previously effective neurostimulation regimen will diminish or simply disappear, which can make diagnosis difficult. Moreover, even after a physician has determined that lead migration has occurred and that the system must be reprogrammed to accommodate the new positions of the electrodes, conventional neurostimulation systems do not provide the physician with information about the movement of an individual lead, such as how far the lead has moved relative to the underlying tissue. This makes reprogramming especially difficult because it relies on trial and error and patient feedback to identify which of the lead electrodes are now aligned with the target neural elements and which are not.

The present inventors have also determined that conventional methods of detecting the relative positions of two or more neurostimulation leads at the time of implantation, as well as at subsequent times, are susceptible to improvement.

SUMMARY OF THE INVENTIONS

Apparatus and methods in accordance with one of the present inventions measure artifactual data about tissue in the vicinity of an implanted lead, such as a neurostimulation lead, to detect lead migration and, in some implementations, to provide information about the lead migration. Such artifactual tissue data includes tissue impedance data and physiologically evoked potential data. Typically, the baseline artifactual data will be measured when the system is providing the desired therapeutic result and the subsequent artifactual data will be measured thereafter. Variations from the baseline artifactual data may be used to indicate that the lead has migrated.

Such apparatus and methods are advantageous for a variety of reasons. For example, the apparatus and methods provide a reliable indication that a particular lead (or leads) in a neurostimulation system has migrated. The present inventions also provide specific information about the migration, such as the magnitude and direction of the migration relative to the underlying tissue, which reduces the difficulty associated with system reprogramming.

Apparatus and methods in accordance with one of the present inventions determine the relative positions of neurostimulation leads by measuring the impedance of tissue between each neurostimulation lead and an electrode that is located in spaced relation to the neurostimulation leads. The measurements may be compared to determine whether one of the neurostimulation leads is a greater distance from the electrode than the other.

Such apparatus and methods are advantageous for a variety of reasons. For example, the apparatus and methods provide a convenient way to differentiate the leads from one another during the post-implantation programming process.

The above described and many other features of the present inventions will become apparent as the inventions become better understood by reference to the following detailed description when considered in conjunction with the accompanying drawings.

BRIEF DESCRIPTION OF THE DRAWINGS

Detailed description of exemplary embodiments of the inventions will be made with reference to the accompanying drawings.

DETAILED DESCRIPTION OF THE EXEMPLARY EMBODIMENTS

This application is related to concurrently filed application Ser. No. 11/096,483, entitled "Apparatus and Methods for Detecting Migration of Neurostimulation Leads."

The following is a detailed description of the best presently known modes of carrying out the inventions. This description is not to be taken in a limiting sense, but is made merely for the purpose of illustrating the general principles of the inventions. The detailed description is organized as follows:

I. Exemplary Neurostimulation Systems
II. Exemplary Lead Migration Detection
III. Exemplary Corrective Measures The section titles and overall organization of the present detailed description are for the purpose of convenience only and are not intended to limit the present inventions.

I. Exemplary Neurostimulation Systems

Figures 1, 1A:
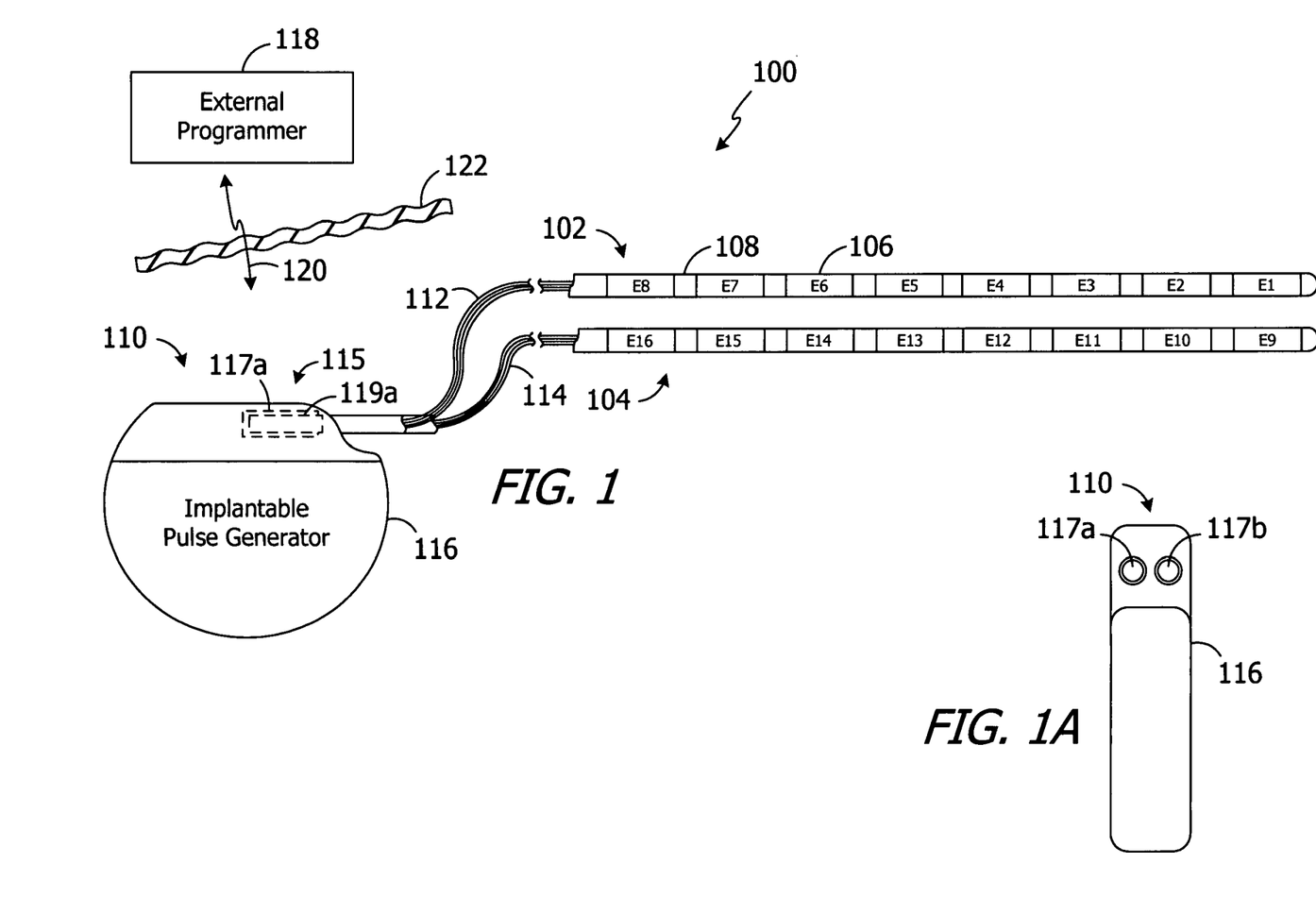
FIG. 1 is a side view of a neurostimulation system in accordance with one embodiment of a present invention.
FIG. 1A is an end view of an implantable pulse generator in accordance with one embodiment of a present invention.

The present inventions have application in a wide variety of neurostimulation systems. Although the present inventions are not so limited, examples of such systems are illustrated in FIGS. 1-5. Referring first to FIGS. 1 and 1A, an exemplary implantable neurostimulation system 100 includes first and second implantable leads 102 and 104. The exemplary leads 102 and 104 are in-line leads and, to that end, both of the leads consist of a plurality of in-line electrodes 106 carried on a flexible body 108. In the illustrated embodiment, there are eight (8) electrodes on lead 102, which are labeled E1-E8, and there are eight (8) electrodes on lead 104, which are labeled E9-E16. The actual number of leads and electrodes will, of course, vary according to the intended application and the present inventions are not limited to any particular numbers of leads and electrodes. The leads 102 and 104 may be implanted into a desired location, such as adjacent to the patient's spinal column, through the use of an insertion needle or other conventional techniques. Once in place, the electrodes 106 may be used to supply stimulation energy to the target neural elements or other target tissue.

The exemplary neurostimulation system 100 illustrated in FIGS. 1 and 1A also includes an implantable pulse generator (IPG) 110 that is capable of directing tissue stimulation energy to each of the electrodes 106. To that end, each of the electrodes 106 on the lead 102 is electrically connected to the IPG 110 by a respective signal wire 112 (some of which are not shown) that extends through, or is imbedded in, the associated flexible body 108. Similarly, the electrodes 106 on the lead 104 are electrically connected to the IPG 110 by respective signal wires 114 (some of which are not shown). The signal wires 112 and 114 are connected to the IPG 110 by way of an interface 115. The interface 115 may be any suitable device that allows the leads 102 and 104 to be removably or permanently electrically connected to the IPG 110. Such an interface may, for example, be an electromechanical connector arrangement including lead connectors 117a and 117b within the IPG 110 that are configured to mate with corresponding connectors (only connector 119a is shown) on the leads 102 and 104. Alternatively, the leads 102 and 104 can share a single connector that mates with a corresponding connector on the IPG. Exemplary connector arrangements are disclosed in U.S. Pat. Nos. 6,609,029 and 6,741,892, which are incorporated herein by reference.

The exemplary IPG 110 includes an outer case 116 that is formed from an electrically conductive, biocompatible material such as titanium and, in some instances, will function as an electrode. The IPG 110 is typically programmed, or controlled, through the use of an external (non-implanted) programmer 118. The external programmer 118 is coupled to the IPG 110 through a suitable communications link, which represented by the arrow 120, that passes through the patient's skin 122. Suitable links include, but are not limited to, radio frequency (RF) links, inductive links, optical links and magnetic links. The programmer 118 or other external device may also be used to couple power into the IPG 110 for the purpose of operating the IPG or replenishing a power source, such as a rechargeable battery, within the IPG. Once the IPG 110 has been programmed, and its power source has been charged or otherwise replenished, the IPG may function as programmed without the external programmer 118 being present.

With respect to the stimulus patterns provided during operation of the exemplary neurostimulation system 100, electrodes that are selected to receive stimulation energy are referred to herein as "activated," while electrodes that are not selected to receive stimulation energy are referred to herein as "non-activated." Electrical stimulation will occur between two (or more) electrodes, one of which may be the IPG case, so that the electrical current associated with the stimulus has a path through the tissue from one or more electrodes configured as anodes to one or more electrodes configured as cathodes, or return electrodes. The return electrode(s) may be one or more of the electrodes 106 on the leads 102 and 104 or may be the IPG case 116. Stimulation energy may be transmitted to the tissue in monopolar or multipolar fashion. Monopolar stimulation occurs when a selected one of the lead electrodes 106 is activated along with the case 116. Bipolar stimulation occurs when two of the lead electrodes 106 are activated. For example, electrode E3 on lead 102 may be activated as an anode at the same time that electrode E11 on lead 104 is activated as a cathode. Tripolar stimulation occurs when three of the lead electrodes 106 are activated. For example, electrodes E4 and E5 on lead 102 may be activated as anodes at the same time that electrode E13 on lead 104 is activated as a cathode. Generally speaking, multipolar stimulation occurs when multiple lead electrodes 106 are activated.

Figures 2, 3:
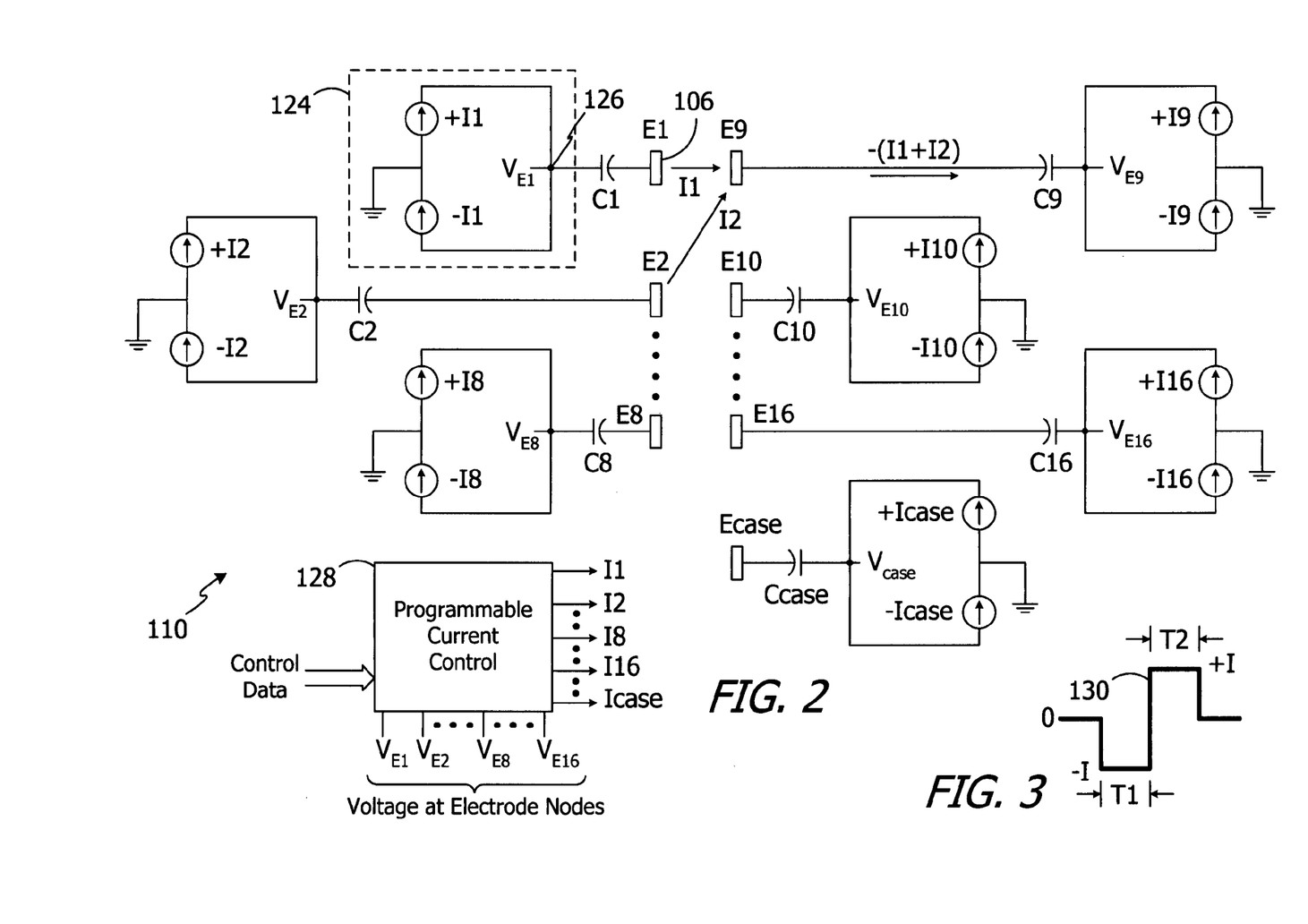
FIG. 2 is a functional block diagram of an implantable pulse generator in accordance with one embodiment of a present invention.
FIG. 3 is an illustration of a stimulation pulse that may be produced by the implantable pulse generator illustrated in FIG. 2.

Turning to FIG. 2, the exemplary IPG 110 has a plurality of dual current sources 124. Each dual current source 124 includes a positive current source that can function as an anode (+I1, +I2, +I3, . . . +Icase) to "source" current to a load, as well as a current source that can function as a cathode (−I1, −I2, −I3, . . . −Icase) to "sink" current from the load, through a common node 126. The load is the tissue that resides between the activated electrodes 106, the wires (and other conductive elements), and the coupling capacitor (C1, C2, C3, . . . Ccase) that connects the associated electrode to the common node 126 of the dual current source 124.

The IPG programming will dictate which of the electrodes, i.e. the lead electrodes 106 and the IPG case 116, will act as sources and sinks at any particular time. To that end, the IPG 110 is provided with a programmable current control circuit 128 that causes selected dual current sources 124 to operate as an anode or a cathode, at specified times, to source or sink current having predetermined amplitude. In the illustrated embodiment, where there are eight (8) electrodes 106 on lead 102 (labeled E1-E8), eight (8) electrodes on lead 104 (E9-E16), and an IPG case 116 that can function as an electrode (labeled Ecase), there are seventeen individually operable dual current sources 124. The control circuit 128, which typically operates in accordance with stored control data that is received from the programmer 118, also turns off the selected dual current sources 124 at specified times. Alternative implementations may, however, employ fewer dual current sources than there are electrodes. Here, at least some of the dual current sources will be connected to more than one electrode through a suitable multiplexer circuit. Alternative implementations may also be configured such that the IPG case 116 only functions as an anode, or such that the IPG case 116 only functions as a cathode The control circuit 128 may, in addition, be used to perform various measurement functions. For example, the control circuit 128 may be used to measure the electrode voltage $V_{E1}$, $V_{E2}, V_{E3} \ldots V_{E16}$ at the output node 126 of each dual current source 124, whether the electrode is activated or non-activated. This allows the electrode voltage at the electrode to be measured which, in turn, facilitates impedance measurements.

The operation of the control circuit 128 may be explained in the context of the following example. Referring to FIG. 2, the control circuit 128 may be used to simultaneously turn on (or enable) the positive current sources in the dual current sources 124 connected to lead electrodes E1 and E2 during time T1. The negative current source in the dual current source 124 connected to lead electrode E9 is also turned on during time T1. All other current sources are off (or disabled) during the time T1. This causes electrodes E1 and E2 to be activated as anodes at the same time that electrode E9 is activated as a cathode. Currents +I1 and +I2 are sourced from electrodes E1 and E2 at the same time that current −I9 is sunk into electrode E9. The amplitudes of the currents +I1 and +I2 may be any programmed values, and the amplitude of the current −I9 should be equal to −(I1+I2). That is, the current that is sourced is equal to the current that is sunk. After time period T1, the control circuit 128 will typically switch the polarities of the electrodes E1, E2 and E9 during a second time period T2 so that the electrodes E1 and E2 will be activated as cathodes and the electrode E9 will be activated as an anode.

Operating the control circuit 128 in this manner produces the biphasic stimulation pulse 130 illustrated in FIG. 3 that is characterized by a first phase (period T1) of one polarity followed by a second phase immediately or shortly thereafter (period T2) of the opposite polarity. The electrical charge associated with the first phase should be equal to the charge associated with the second phase to maintain charge balance during the stimulation, which is generally considered an important component of stimulation regimes, although this is not required by the present inventions. Charge balance of the biphasic stimulation pulse 130 may be achieved by making the amplitudes of the first and second phases, as well as the periods T1 and T2, substantially equal. Charge balance may also be achieved using other combinations of phase duration and amplitude. For example, the amplitude of the second phase may be equal to one-half of the amplitude of the first phase and the period T2 may be equal to twice the period T1.

Figures 4, 5:
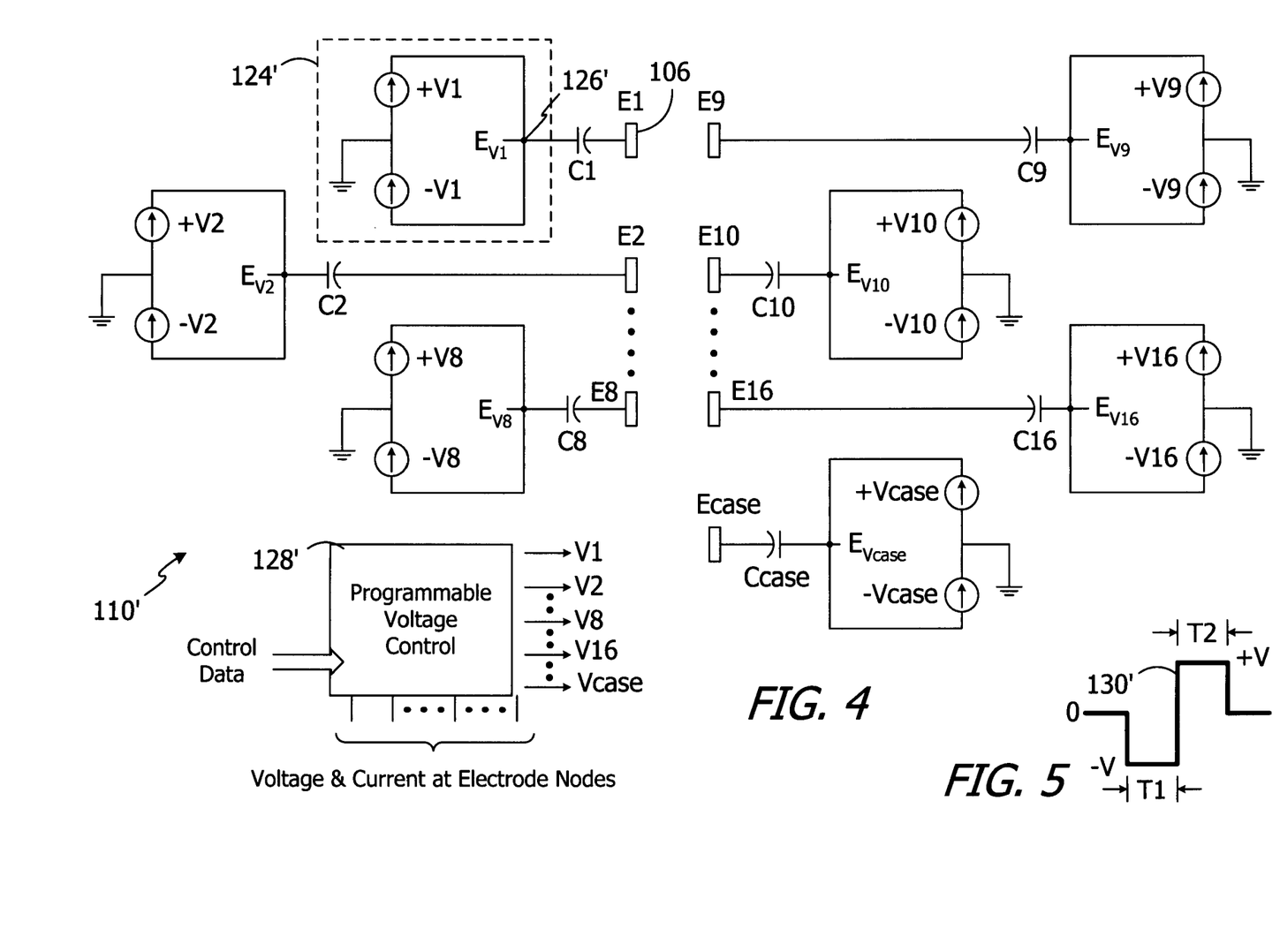
FIG. 4 is a functional block diagram of an implantable pulse generator in accordance with one embodiment of a present invention.
FIG. 5 is an illustration of a stimulation pulse that may be produced by the implantable pulse generator illustrated in FIG. 4.

Neurostimulation systems in accordance with the present inventions may also employ the alternative IPG 110' illustrated in FIG. 4, which includes a plurality of dual voltage sources 124' that are respectively connected to the lead electrodes E1-E16 and the IPG case electrode Ecase. Each dual voltage source 124' applies a programmed voltage to the associated electrode when turned on by way of a node 126' and a coupling capacitor (C1, C2, C3, .... Ccase). Alternative implementations may, however, employ fewer dual voltage sources than there are electrodes. Here, at least some of the dual voltage sources will be connected to more than one electrode through a suitable multiplexer circuit. A programmable voltage control circuit 128' controls each of the dual voltage sources 124' and specifies the amplitude, polarity and duration of the voltage that is applied to the electrodes.

The dual voltage sources 124' and control circuit 128' may be used to produce the biphasic stimulation pulse 130' illustrated in FIG. 5 that is characterized by a first phase (period T1) of one polarity followed by a second phase immediately or shortly thereafter (period T2) of the opposite polarity applied between any two electrodes. Charge balance of the biphasic stimulation pulse 130' may be achieved by making the amplitudes of the first and second phases, as well as the periods T1 and T2, equal. Charge balance may also be achieved using other combinations of phase duration and amplitude. For example, the amplitude of the second phase may be equal to one-half of the amplitude of the first phase and the period T2 may be equal to twice the period T1. The control circuit 128' may also be used to measure the current flowing to or from each electrode, whether the electrode is activated or not, as well as electrode voltage ($E_{V1}$-$E_{V16}$) appearing at the common node 126' of each non-activated dual voltage source 124'. These current and voltage measurements also facilitate impedance measurements.

Additional details concerning the above-described and other IPGs may be found in U.S. Pat. No. 6,516,227 and U.S. Pub. App. 2003/0139781, which are incorporated herein by reference. It also should be noted that the block diagrams illustrated in FIGS. 2 and 4 are functional diagrams, and are not intended to limit the present inventions to any particular IPG circuitry.

II. Exemplary Lead Migration Detection

As noted above, neurostimulation systems in accordance with the present inventions are capable of detecting post-implantation migration of the leads 102 and 104 (i.e. movement of the leads relative to the underlying tissue) and, in some implementations, are also capable of providing information about the migration. Generally speaking, the present migration detection processes employ artifactual tissue measurements, such as tissue impedance measurements or evoked potential measurements, to detect migration of the leads 102 and 104. The data gleaned from the measurements may be stored and processed by the IPG control circuit 128 (or 128'), by the external programmer 118, by some combination thereof, or the like. Additionally, the artifactual tissue measurements (e.g., tissue impedance measurements and evoked potential measurements) allow lead migration to be detected on an individual basis relative to the underlying tissue, as opposed to detecting migration of one lead relative to the other. Accordingly, the processes described herein may be employed in neurostimulation systems with a single lead as well as neurostimulation systems, such as the exemplary system 100, with a plurality of leads.

Turning first to tissue impedance, the impedance of tissue adjacent to the lead electrodes 106 may be measured and monitored in order to provide an indication that a lead has migrated. The tissue impedance measured at the lead electrodes 106 depends on the tissue in vicinity of the electrode (i.e. tissue within about 1 mm of the electrode) as opposed to all of the tissue located between electrodes on adjacent leads. Such tissue includes fat, collagen, bone, ligament, the white and gray matter of the spinal cord, and dura. The measured impedance will also typically vary from electrode to electrode along the length of a lead.

Figure 6A:
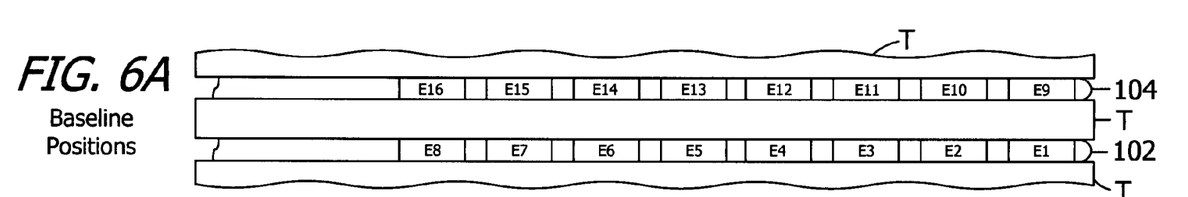
FIGS. 6A and 6B are plan views showing exemplary implantable leads in baseline positions and subsequent positions.

Referring first to FIG. 6A, after the leads 102 and 104 have been properly positioned within tissue T ("proper" positioning varies from patient to patient), the impedance of the tissue adjacent to each of the electrodes 106 (individually identified as E1-E16) may be measured. This may be accomplished in a variety of ways. For example, impedance may be determined by sourcing current from the IPG outer case 116, which functions as electrode Ecase (FIG. 2), and sinking current at a selected one of the electrodes E1-E16 at a predetermined voltage. Given that most of the drop will occur at the smaller electrode, and that the lead electrodes 106 are much smaller than the IPG outer case 116, it can be assumed that the measured impedance between the selected lead electrode and the outer case is primarily due to the impedance of the tissue adjacent to the selected lead electrode. It should be noted that the current used for impedance measurements is a sub-threshold current pulse (e.g. 1 mA for 20 μs) that will not cause stimulation or substantially drain the IPG battery. This process may be repeated for each of the electrodes E1-E16. Alternatively, an electrode that is sutured anywhere in or on the patient's body and, preferably, that is larger than the lead electrodes, may be used in place of the case IPG outer case for these measurements.

Preferably, the impedances will be measured at each of the electrodes E1-E16 immediately after the lead has been implanted and the neurostimulation system IPG control circuit 128 (or 128') has been programmed to produce the desired therapeutic effect. Such an impedance measurement, which is referred to herein as a "baseline impedance measurement," may consist of a single set of measurements at electrodes E1-E16 or a number of sets of measurement at the electrodes that are averaged together on an electrode-by-electrode basis. Exemplary plots of the impedance at each electrode E1-E8 on lead 102 and each electrode E9-E16 on lead 104 are shown with solid lines in FIG. 7. Baseline impedance measurements may also be trended in the manner described below.

Impedance measurements are also taken at each of the electrodes E1-E16 at various times after the baseline impedance measurement has been established. For example, impedance measurements may be taken at a periodic check-up or in response to an indication from the patient that the neurostimulation system is no longer providing the same level of therapeutic effect that it did when the baseline impedance measurement was taken. Such an impedance measurement is referred to herein as a "subsequent impedance measurement" and may consist of a single set of measurements at electrodes E1-E16 or a number of sets of measurements at the electrodes that are averaged together on an electrode-by-electrode basis. The subsequent impedance measurement is compared to the baseline impedance measurement to determine whether or not the measurements have changed. A change may indicate that the associated lead has migrated. A feature comparison analysis, such as a peak comparison, a slope comparison, or the like, may be used to determine the magnitude and direction of any detected lead migration. One example of a mathematical technique that may be used to implement the feature comparison analysis is a cross-correlation function. Other suitable algorithms may also be used to implement the feature comparison analysis.

Baseline impedance measurements include non-trended baseline impedance measurements, where the baseline impedance values do not change over time, and trended baseline impedance measurements, where the baseline impedance values are adjusted so as to account for factors such as tissue necrosis and fibrosis that cause the measured impedance to change slowly over time, as compared to lead migration, which tends to produce abrupt changes in impedance measurements. A trended baseline impedance value may be established per the following examples. When a subsequent impedance measurement is substantially similar to the baseline impedance measurement (based on, for example, a feature comparison analysis), it may be assumed that the difference in the impedance measurement is not due to lead migration. The substantially similar subsequent impedance measurement may then be used to establish a new baseline impedance measurement value. This may be accomplished by substituting the substantially similar subsequent impedance measurement for the original baseline impedance measurement or by averaging the two. Additionally, or alternatively, as additional subsequent impedance measurements are taken over time, a moving average process may be used to establish the trended baseline impedance value.

Figure 6B:
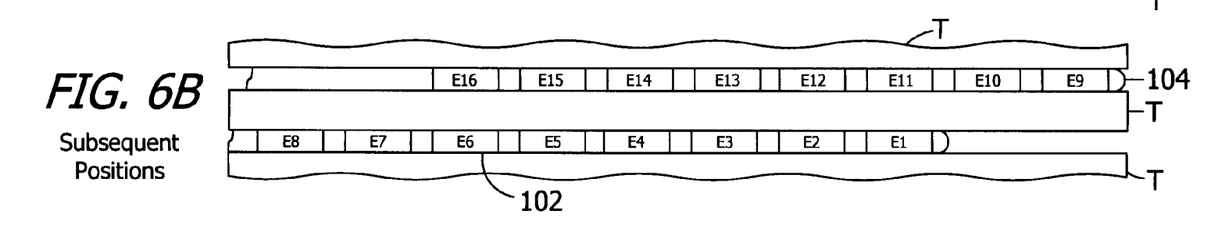
Figure 7:
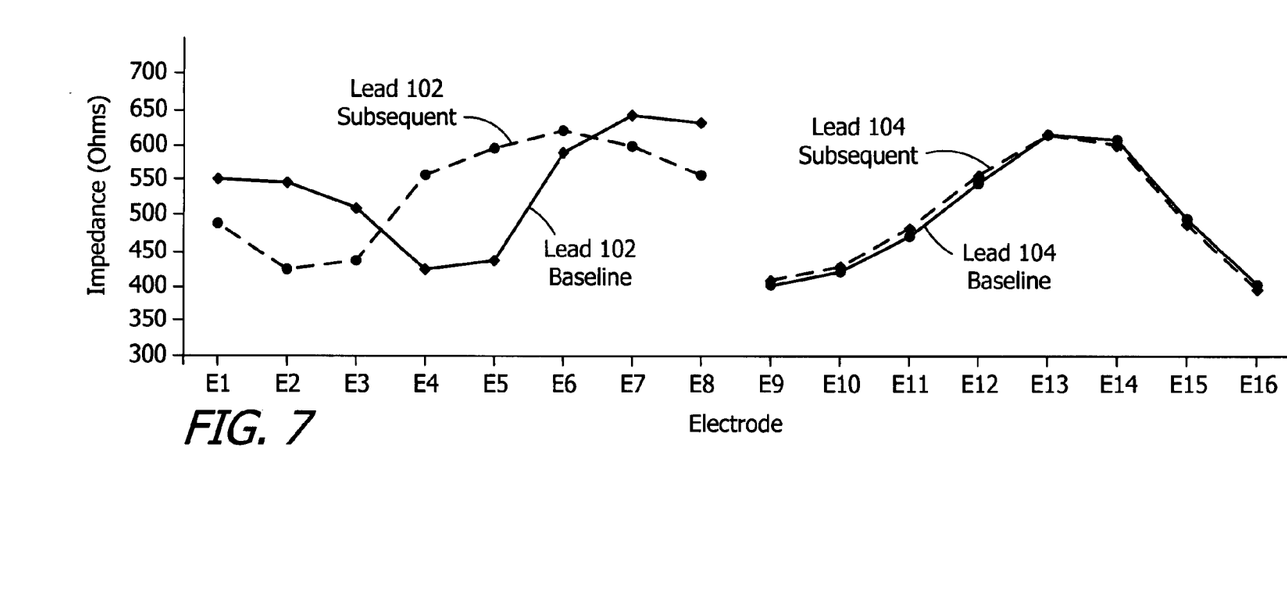
FIG. 7 is a graph showing impedance measurements taken when the implantable leads are in the positions illustrated in FIGS. 6A and 6B.

Exemplary positions of the leads 102 and 104 at the time of a subsequent impedance measurement are illustrated in FIG. 6B and the corresponding plots of the subsequent impedance measurement at each of the electrode E1-E16 is shown with dashed lines in FIG. 7. Referring first to lead 102, the plot of the subsequent impedance measurement is clearly different than the plot of the baseline impedance measurement. This difference provides an indication that the lead 102 may have moved relative to the tissue in the vicinity of the lead. Additional information that can confirm movement may be obtained by comparing the plots, or the before and after tissue impedance measurements at each electrode E1-E8, to one another. In the illustrated example, the subsequent tissue impedance measurements taken at electrodes E2 and E3 are essentially the same as the baseline tissue impedance measurements taken at electrodes E4 and E5, respectively. From this, it may be inferred that the electrodes E2 and E3 have moved to the locations originally occupied by electrodes E4 and E5, respectively, and that the lead 102 has moved a distance corresponding to two electrodes 106. If, for example, there is a 4 mm electrode-to-electrode spacing, it could be inferred that the lead 102 moved 8 mm.

Turning to lead 104, the plot of the subsequent impedance measurement is essentially the same as the plot of the baseline impedance measurement. This provides an indication that the lead 104 has not moved relative to the tissue.

Other information may also be gleaned from comparisons of the subsequent impedance measurement and the baseline impedance measurement. For example, in some instances, the lowest of the baseline impedance measurements or an average of all of the baseline impedance measurements may be used to establish a "nominal impedance value." If the nominal impedance value increases after the lead 102 has moved, it may be inferred that the distance between the lead 102 and the IPG outer case 116 has increased. Similarly, if the nominal impedance value decreases after the lead 102 has moved, it may be inferred that the distance between the lead 102 and the IPG outer case 116 has decreased.

Impedance measurements may also be used to determine information that is needed prior to programming or reprogramming. The mean impedance value for each lead 102 and 104 (i.e. the average value of each of the impedance measurements taken at the electrodes 106 on the lead) will typically be greater for the lead that is the greatest distance from the IPG case 116 (or 116'). As such, the mean impedance measurements may also be used to determine the relative positions of the leads 102 and 104 with respect to the IPG 110 (or 110'). This relative position determination will typically be made when the leads 102 and 104 are initially implanted into the patient to assist with the programming process, but may also be made at other times if needed.

In the SCS context, the leads 102 and 104 may be implanted, for example, anywhere from the cervical area down to the sacral area. The leads may be positioned such that one lead is in one area and one lead is in a different area, such that both leads are located in the same area and are aligned with one another with respect to their distance from the IPG case 116 (or 116'), or such that both leads are located in the same area, but are staggered with respect to their distance from the IPG case. As noted above, it may be inferred that the lead which produces the largest mean impedance value is the greatest distance from the case. If, for example, the IPG 110 (or 110') is implanted in the upper region of a buttock, one lead is positioned in the thoracic area and one lead is positioned in the cervical area, then it may be inferred that the lead which produces the larger mean impedance value is in the cervical area. If both of the leads are positioned within the same area (e.g. the cervical area or the thoracic area), it may be inferred that the leads are aligned with one another if the mean impedance values are substantially equal, or it may be inferred that the leads are staggered and that the lead with the greater value is a greater distance from the IPG 110 (or 110') if the mean impedance values are substantially different.

Tissue impedance measurements may also be taken in essentially continuous fashion after the baseline impedance measurement has been established. For example, the therapeutic pulses in a SCS program are typically 1 ms in duration and are supplied at a frequency of 50 Hz. There are, therefore, 19 ms between each therapeutic pulse during which time sub-therapeutic pulses may be provided for impedance measurement purposes. The continuously-taken subsequent impedance measurements may be compared to the baseline impedance measurement as they are taken in order to provide a real time indication that a lead has moved. Once such a determination has been made, corrective measures such as those discussed in Section III below may be automatically undertaken or the patient may simply be advised of the situation so that he or she can relay this information to a physician.

Figure 8A:
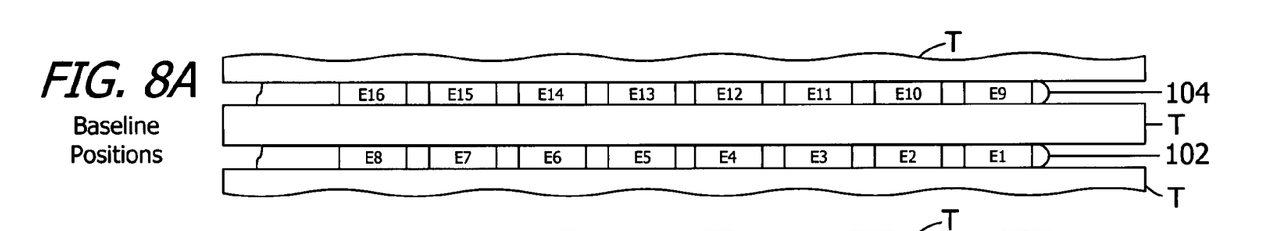
FIGS. 8A and 8B are plan views showing exemplary implantable leads in baseline positions and subsequent positions.

Evoked potential measurements (also referred to herein as "physiologically evoked potential measurements"), which generally involve providing a stimulation pulse to nerves at one electrode and measuring the generated action potential at another electrode, may also be used to determine whether or not a lead has migrated relative to the underlying tissue in the vicinity of the lead. Referring first to FIG. 8A, baseline evoked potential measurements may be taken after the implantable leads 102 and 104 have been properly positioned adjacent to the tissue T ("proper" positioning varies from patient to patient). With respect to lead 102, a stimulation pulse will be supplied by electrode E1 to the adjacent tissue and the resulting action potential will generate a measurable deviation in the voltage that the programmable controller 128 sees at electrode E2 for a finite time that can be measured (or "read"). A suitable stimulation pulse for this purpose is, for example, 4 mA for 200 µs. Such stimulation is preferably supra-threshold, but not uncomfortable. This process may be performed once, or many times and averaged (e.g. 100 times), so that "baseline" stimulate-E1/evoked-potential-at-E2 data may be generated and measured, and then plotted in the manner illustrated for example in FIG. 9A (note the solid line). The deviation in voltage caused by the evoked potential due to the stimulation pulse at electrode E1 could also be sequentially measured at electrodes E3-E8 (either once or many times and averaged) in order to provide additional baseline data and plots. Electrodes E2-E9 may also be used to supply stimulation pulses and evoked potentials may be measured at one or more of the other electrodes on lead 102.

Turning to lead 104, a stimulation pulse may be supplied by electrode E9 to the adjacent tissue and the resulting evoked potential measured at electrode E10 and, if desired, sequentially measured at electrodes E11-E16. Again, this process may be performed once or many times and averaged. The baseline stimulate E9-evoked potential at E10 data is shown with a solid line in FIG. 9B. Electrodes E10-E16 may also be used to supply stimulation pulses and evoked potentials may be measured at one or more of the other electrodes on lead 104.

It should be noted that evoked potentials may also/instead be measured at additional or other electrodes 106 because the action potential may propagate in a variety of directions depending on what nerves are stimulated and where they go. For example, evoked potentials may be measured at the electrodes 106 on the non-stimulating lead in addition to (or instead of) the electrodes on the stimulating lead. The deviation in voltage caused by the evoked potential due to the stimulation pulse at an electrode 106 on lead 102 could, for example, also be measured at one or more of the electrodes on lead 104 (either once or many times and averaged) in order to provide additional baseline data and plots. Similarly, the deviation in voltage caused by the evoked potential due to the stimulation pulse at an electrode 106 on lead 104 could also be measured at one or more of the electrodes on lead 102 (either once or many times and averaged) in order to provide additional baseline data and plots. There may also be instances where it is desirable to measure the deviation in voltage caused by the evoked potential at the stimulating electrode. For example, the deviation in voltage caused by the evoked potential due to a stimulation pulse at electrode E1 could be measured at electrode E1, and the deviation in voltage caused by the evoked potential due to a stimulation pulse at electrode E9 could be measured at electrode E9.

Evoked potential measurements may also be taken at various times after the baseline evoked potential measurements have been established for each of the leads 102 and 104. For example, evoked potential measurements may be taken at a periodic check-up or in response to an indication from the patient that the neurostimulation system is no longer providing the same level of therapeutic effect that it did when the baseline measurements were taken. Such evoked potential measurements are referred to herein as "subsequent" evoked potential measurements. The same stimulation pulse or one that provides a grossly equivalent intensity of stimulation effect (as identified by the patient) that was supplied to tissue during the baseline measurement (e.g. 4 mA for 200 µs) will be supplied by the same electrode and the deviation in the voltage will be measured at the same electrode (or electrodes), either once or many times and averaged, so that subsequent evoked potential data may be generated, measured and plotted.

For example, subsequent stimulate-E1/evoked-potential-at-E2 data may be generated, measured, and plotted to determine whether there has been migration of lead 102, and subsequent stimulate E9-evoked potential at E10 data may be generated, measured and plotted to determine whether there has been migration of lead 104. If the data produces the same evoked potential plots, or if the plots are within some acceptable deviation therefrom, then it can be assumed that the leads have not moved (or have moved an acceptably small amount). An unacceptable deviation may, for example, be defined as an abrupt or significant short-term change from the baseline evoked potential data. It is likely that changes in the evoked potential data due to factors such as necrosis or fibrosis change relatively slowly, whereas migration is more likely to cause an abrupt change in the data. Accordingly, the baseline evoked potential measurements may include non-trended baseline evoked potential measurements, where the baseline evoked potential values do not change over time, and trended baseline evoked potential measurements, where the baseline evoked potential values are adjusted so as to account for factors such as tissue necrosis and fibrosis. The subsequent evoked potential measurements may be used in the manner described above in the context of impedance measurements to establish trended baseline evoked potential values.

If, on the other hand, the subsequent evoked potential data is different (e.g., exhibits an abrupt or significant short term change from the baseline evoked potential data) for one or both of the leads, or if there is no measurable evoked potential at the electrode where the evoked potential was measured for one or both of the leads, it can be assumed that the lead (or leads) associated with the different data has moved. For instance, if it is assumed that lead 102 has moved, the assumption may be checked by measuring the evoked potentials at electrodes E3-E8 on lead 102 (either once or many times and averaged). If the subsequent plots associated with the evoked potentials at electrodes E3-E8 were the same as, or some acceptable deviation from, the baseline plots, it may be assumed that the lead 102 has not moved and that there has been a change in conditions at electrode E2. The assumption may also be checked by measuring the evoked potentials at electrode E1 on lead 102 and/or electrodes E9-E16 on lead 104 (either once or many times and averaged) if these electrodes were used for the baseline measurements taken with respect to stimulation at electrode E1. Here too, if the subsequent plots are the same as, or some acceptable deviation from, the baseline plots, it may be assumed that lead 102 has not moved. With respect to the tissue adjacent to electrode E2, the difference in evoked potentials that is not due to lead movement could be due to scarring, necrosis or fat build up. Alternatively, there could be damage to electrode E2.

The same checking procedure may also be performed with respect to lead 104. Specifically, the evoked potentials resulting from stimulation at electrode E9 on lead 104 may be measured at electrodes E11-E16. Additionally or alternatively, if they were part of the baseline measurement process, the evoked potentials may be measured at electrode E9 on lead 104 and/or electrodes E1-E8 on lead 102.

Figure 8B:
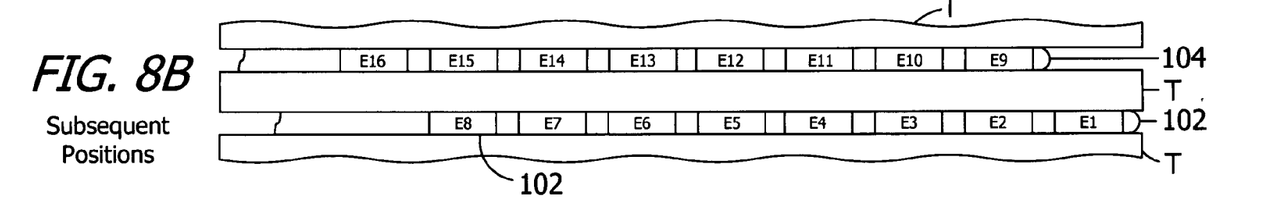
Figure 9A:
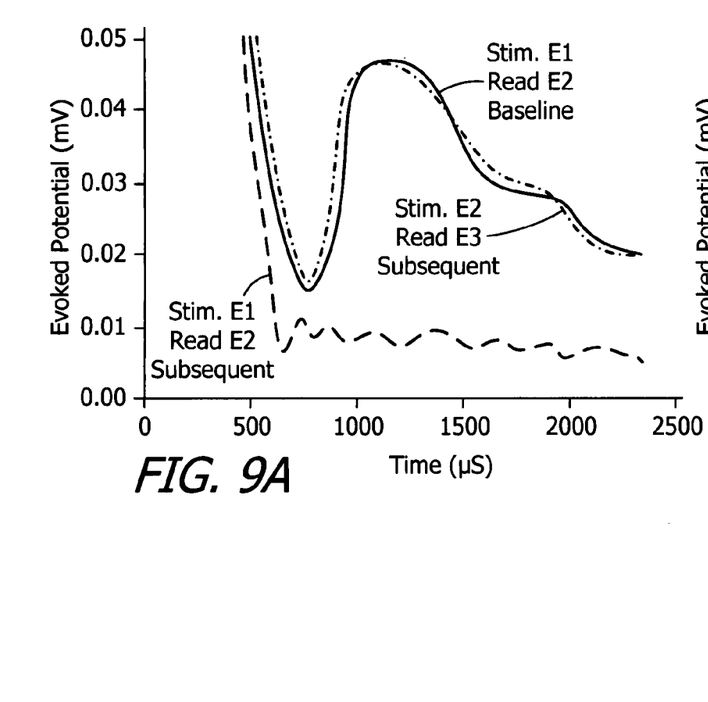
FIG. 9A is a graph showing evoked potential measurements taken at one of the implantable leads when the lead is in the positions illustrated in FIGS. 8A and 8B.
Figure 9B:
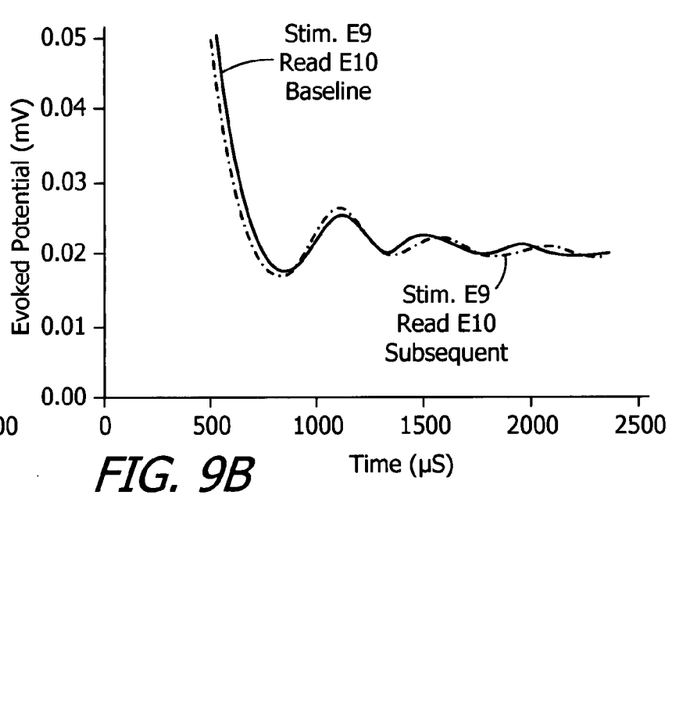
FIG. 9B is a graph showing evoked potential measurements taken at the other of the implantable leads when the lead is in the positions illustrated in FIGS. 8A and 8B.

Referring to FIGS. 8B, 9A and 9B, lead 102 is shown having moved a distance corresponding to one electrode and, accordingly, the subsequent stimulate-E1/evoked-potential-at-E2 data is different. Lead 104, on the other hand, has not moved and the subsequent stimulate E9-evoked potential at E10 data is essentially the same.

Evoked potentials may also be used to determine the direction and magnitude of the movement. For instance, a feature comparison analysis (implemented by, for example, a cross-correlation technique) may be used to determine the magnitude and direction of any shift. Here, stimulation energy is individually provided to electrodes other than the originally stimulating electrode on the lead that has moved, and the evoked potentials are measured at the other electrodes. The object is to identify an electrode that produces similar evoked potential data as was produced by an electrode used in the baseline measurements. If such an electrode is identified, it may be assumed that it now occupies the position of the electrode that was used to produce the baseline data. With respect to the movement of lead 102, and as illustrated FIGS. 8B and 9A, the stimulate-at-E2/evoked-potential-at-E3 plot closely corresponds to the baseline stimulate-at-E1/evoked-potential-at-E2 plot (FIG. 9) because electrodes E2 and E3 are located in the positions previously occupied by electrodes E1 and E2, respectively.

Figure 10:
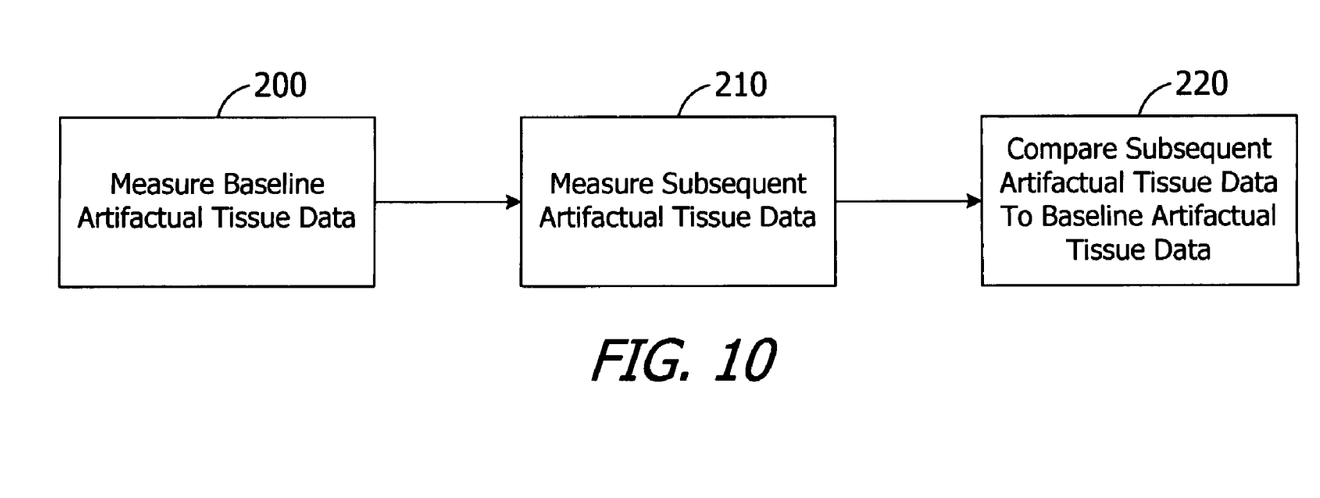
FIG. 10 is a flow chart summarizing various processes in accordance with the present inventions.

A flow chart that summarizes both of the methods described above is presented in FIG. 10. In step 200, baseline artifactual tissue data, such as tissue impedance data or evoked potential data, is measured with one of the leads. Next, in step 210, artifactual tissue data is measured at one or more subsequent times with the same lead. Finally, in step 220, the subsequent artifactual tissue data is compared to the baseline artifactual data (which may included non-trended baseline artifactual data and/or trended baseline artifactual data) to determine whether the lead has moved. This process may be repeated with each lead.

III. Exemplary Corrective Measures

The corrective action that may be taken after it has been determined that one or more of the leads in a neurostimulation system (such as an SCS system) has moved generally falls into two categories—(1) surgical removal or repositioning and (2) reprogramming. Surgical removal or repositioning will typically be employed when it has been determined that one or more of the leads has moved too far to make reprogramming a viable option. If, for example, the therapeutic regimen required that an electrode be located in the baseline location of electrode E2 on lead 102 (FIG. 6A), the therapeutic regimen could not be performed once lead 102 migrated to the location shown in FIG. 6B because there is no longer any electrode in that location. Surgical removal may also be required if one or more of the electrodes are damaged or fail.

With respect to reprogramming, individualized information concerning the actual movement (or lack of movement) of each lead will allow the reprogramming to proceed in a far more efficient manner than would be the case if the entity tasked with reprogramming (i.e. a physician or the neurostimulation system) merely knew that at least one of the leads has moved because the relative positions of the leads has changed. Assuming for example that the leads 102 and 104 illustrated in FIG. 6A were employed in a therapeutic regimen that involve sourcing and sinking stimulation pulses from electrodes E4, E5 and E6 on lead 102 and electrodes E13 and E14 on lead 104. After lead 102 moved to the position illustrated in FIG. 6B, and it was determined by the present inventions that only lead 102 moved and that lead 102 moved toward the IPG 110 a distance corresponding to two electrodes, the therapeutic regimen may reprogrammed by simply substituting electrodes E2, E3 and E4, respectively, for electrodes E4, E5 and E6.

Reprogramming may be performed automatically or by a clinician. Automatic reprogramming, which is especially useful when lead migration is being continuously monitored, could be truly automatic (i.e. it would happen without the patient's knowledge). Alternatively, the IPG 110 could provide the patient with an indication that at least one lead has moved and give the patient the option of trying the automatically reprogrammed stimulation regimen or simply reporting the lead migration to the clinician. Reprogramming by the clinician, either in response to a notification from the IPG 110 or patient complaint, would typically involve allowing the external programmer 118 to modify (or simply suggest a modification of) the therapeutic regimen based on the lead migration data from the IPG 110. Alternatively, the lead repositioning is recorded for the clinician to review for use during reprogramming, thereby reducing the amount of clinician time (and expense) required to reprogram the therapeutic regimen as well as the likelihood that an expensive fluoroscopic procedure will be required.

Although the inventions disclosed herein have been described in terms of the preferred embodiments above, numerous modifications and/or additions to the above-described preferred embodiments would be readily apparent to one skilled in the art. By way of example, but not limitation, the present inventions include neurostimulation systems that also comprise at least one neurostimulation lead. It is intended that the scope of the present inventions extend to all such modifications and/or additions and that the scope of the present inventions is limited solely by the claims set forth below.

We claim:

1. A method to determine whether a neurostimulation lead has migrated, comprising:
    measuring the impedance of tissue in the vicinity of an electrode on the neurostimulation lead to establish a baseline impedance value;
    measuring the impedance of the tissue in the vicinity of the electrode at a subsequent time to establish a subsequent impedance value;
    determining whether the neurostimulation lead has migrated by comparing the subsequent impedance value to the baseline impedance value; and
    creating a trended baseline impedance value based on the baseline impedance value.

2. A method as claimed in claim 1, wherein
    the neurostimulation lead includes a plurality of electrodes;
    measuring the impedance of tissue to establish a baseline impedance value comprises measuring the impedance of the tissue in the vicinity of multiple electrodes to establish respective baseline impedance values;
    measuring the impedance of the tissue to establish a subsequent impedance value comprises measuring the impedance of the tissue in the vicinity of each of the multiple electrodes at a subsequent time to establish respective subsequent impedance values; and
    determining whether the neurostimulation lead has migrated comprises comparing the subsequent impedance values to the baseline impedance values.

3. A method as claimed in claim 2, wherein determining whether the neurostimulation lead has migrated further comprises determining the direction and magnitude of the migration.

4. A method as claimed in claim 3, wherein determining the direction and magnitude of the migration comprises performing a feature comparison analysis.

5. A method as claimed in claim 1, wherein measuring the impedance of tissue in the vicinity of an electrode comprises sourcing current into tissue at an implantable pulse generator and sinking the current at the electrode.

6. A method as claimed in claim 1, wherein measuring the impedance of tissue in the vicinity of an electrode comprises sourcing current into tissue at an implantable pulse generator and sinking the current at the electrode in between therapeutic pulses supplied by the implantable pulse generator to the electrode.

7. A method as claimed in claim 1, further comprising taking corrective action in response to a determination that the neurostimulation lead has migrated.

8. A method as claimed in claim 7, wherein taking corrective action comprises reprogramming a therapeutic regimen in response to a determination that the neurostimulation lead has migrated.

9. A method as claimed in claim 1, wherein the trended baseline impedance value is based on a difference between the baseline impedance value and the subsequent impedance value.

10. A method as claimed in claim 9, wherein the trended baseline impedance value is created by replacing the baseline impedance value with a new baseline impedance value if the difference is relatively small, and maintaining the baseline impedance value if the difference is relatively large.

11. A method as claimed in claim 10, wherein the new baseline impedance value is the subsequent baseline impedance value.

12. A method as claimed in claim 10, wherein the new baseline impedance value is an average of the baseline impedance value and the subsequent baseline impedance value.

13. A method as claimed in claim 1, wherein the trended baseline impedance value is a moving average that includes the baseline impedance value and the subsequent baseline impedance value.

14. A neurostimulation system for use with an implantable lead including at least one lead electrode, the neurostimulation system comprising:
    a pulse generator including a lead connector;
    circuitry, operably connected to the lead connector, to measure the impedance of tissue in the vicinity of the at least one lead electrode to establish a baseline impedance value and measure the impedance of the tissue in the vicinity of the at least one lead electrode at a subsequent time to establish a subsequent impedance value; and
    circuitry to determine whether the implantable lead has migrated by comparing the subsequent impedance value to the baseline impedance value, and to create a trended baseline impedance value based on the baseline impedance value.

15. A neurostimulation system as claimed in claim 14, wherein
    the at least one lead electrode comprises a plurality of lead electrodes;
    the circuitry to measure comprises circuitry to measure the impedance of the tissue in the vicinity of multiple lead electrodes to establish respective baseline impedance values and to measure the impedance of the tissue in the vicinity of each of the multiple lead electrodes at a subsequent time to establish subsequent impedance values; and
    the circuitry to determine comprises circuitry to determine whether the implantable lead has migrated by comparing the subsequent impedance values to the baseline impedance values.

16. A neurostimulation system as claimed in claim 14, wherein the circuitry to determine comprises circuitry to determine the direction and magnitude of the migration.

17. A neurostimulation system as claimed in claim 14, further comprising:
    an electrode associated with the pulse generator;
    wherein the circuitry to measure comprises circuitry to source current into tissue at the electrode associated with the pulse generator and sink the current at the at least one lead electrode.

18. A neurostimulation system as claimed in claim 17, wherein the electrode associated with the pulse generator comprises a pulse generator case.

19. A neurostimulation system as claimed in claim 14, wherein the pulse generator comprises an implantable pulse generator and the circuitry to determine is located within the implantable pulse generator.

20. A neurostimulation system as claimed in claim 14, further comprising:
- at least one external device that communicates with the implantable pulse generator;
- wherein the circuitry to determine is located in the at least one external device.

21. A neurostimulation system as claimed in claim 14, further comprising circuitry to supply therapeutic pulses in accordance with a programmed therapeutic regimen and to adjust the programmed therapeutic regimen in response to a determination that the implantable lead has migrated.

22. A neurostimulation system as claimed in claim 21, wherein the at least one lead electrode comprises a plurality of lead electrodes, the neurostimulation system further comprising circuitry to adjust which of the plurality of lead electrodes receives therapeutic pulses in response to a determination that the implantable lead has migrated.

23. A neurostimulation system as claimed in claim 14, wherein the trended baseline impedance value is based on a difference between the baseline impedance value and the subsequent impedance value.

24. A neurostimulation system as claimed in claim 23, wherein the trended baseline impedance value is created by replacing the baseline impedance value with a new baseline impedance value if the difference is relatively small, and maintaining the baseline impedance value if the difference is relatively large.

25. A neurostimulation system as claimed in claim 24, wherein the new baseline impedance value is the subsequent baseline impedance value.

26. A neurostimulation system as claimed in claim 24, wherein the new baseline impedance value is an average of the baseline impedance value and the subsequent baseline impedance value.

27. A neurostimulation system as claimed in claim 14, wherein the trended baseline impedance value is a moving average that includes the baseline impedance value and the subsequent baseline impedance value.

\* \* \* \* \*